United States Patent [19]

Warnow

[11] 4,172,467
[45] Oct. 30, 1979

[54] RESPIRATOR VALVE FOR RESPIRATORS

[75] Inventor: Detlef Warnow, Lubeck, Fed. Rep. of Germany

[73] Assignee: Drägerwerk Aktiengesellschaft, Fed. Rep. of Germany

[21] Appl. No.: 840,957

[22] Filed: Oct. 11, 1977

[30] Foreign Application Priority Data

Oct. 9, 1976 [DE] Fed. Rep. of Germany ....... 2645675

[51] Int. Cl.² .............................................. A62B 7/04
[52] U.S. Cl. ................................ 137/494; 128/142.2; 137/DIG. 9
[58] Field of Search ..................... 128/142.2; 137/494, 137/DIG. 9

[56] References Cited

U.S. PATENT DOCUMENTS 3,070,108  12/1962  Fischer .......................... 137/DIG. 9
3,724,482  4/1973  Ekstrom ....................... 128/142.2 X

FOREIGN PATENT DOCUMENTS 467507  12/1951  Italy ................................... 137/DIG. 9

Primary Examiner—Robert G. Nilson
Attorney, Agent, or Firm—McGlew and Tuttle

[57] ABSTRACT

A respirator valve for respirators with a pressure-responsive control of the breathing pulses of a patient, comprises, a valve housing which has a pressure chamber therein with a connecting breathing line to the patient. First and second control diaphragms close respective sides of the pressure chamber and are flexible in response to pressure variations in the pressure chamber. A connecting member disposed between the diaphragms is moved by the flexing of the diaphragms so as to operate a lever mechanism for shifting a valve member to open or close a valve seat in a connecting line to a pressurized breathing gas for supplying the breathing gas into the pressure chamber and into the patient in accordance with variations in the patient's efforts to inhale and to cause pressure variations in the pressure chamber to actuate the diaphragms.

6 Claims, 1 Drawing Figure

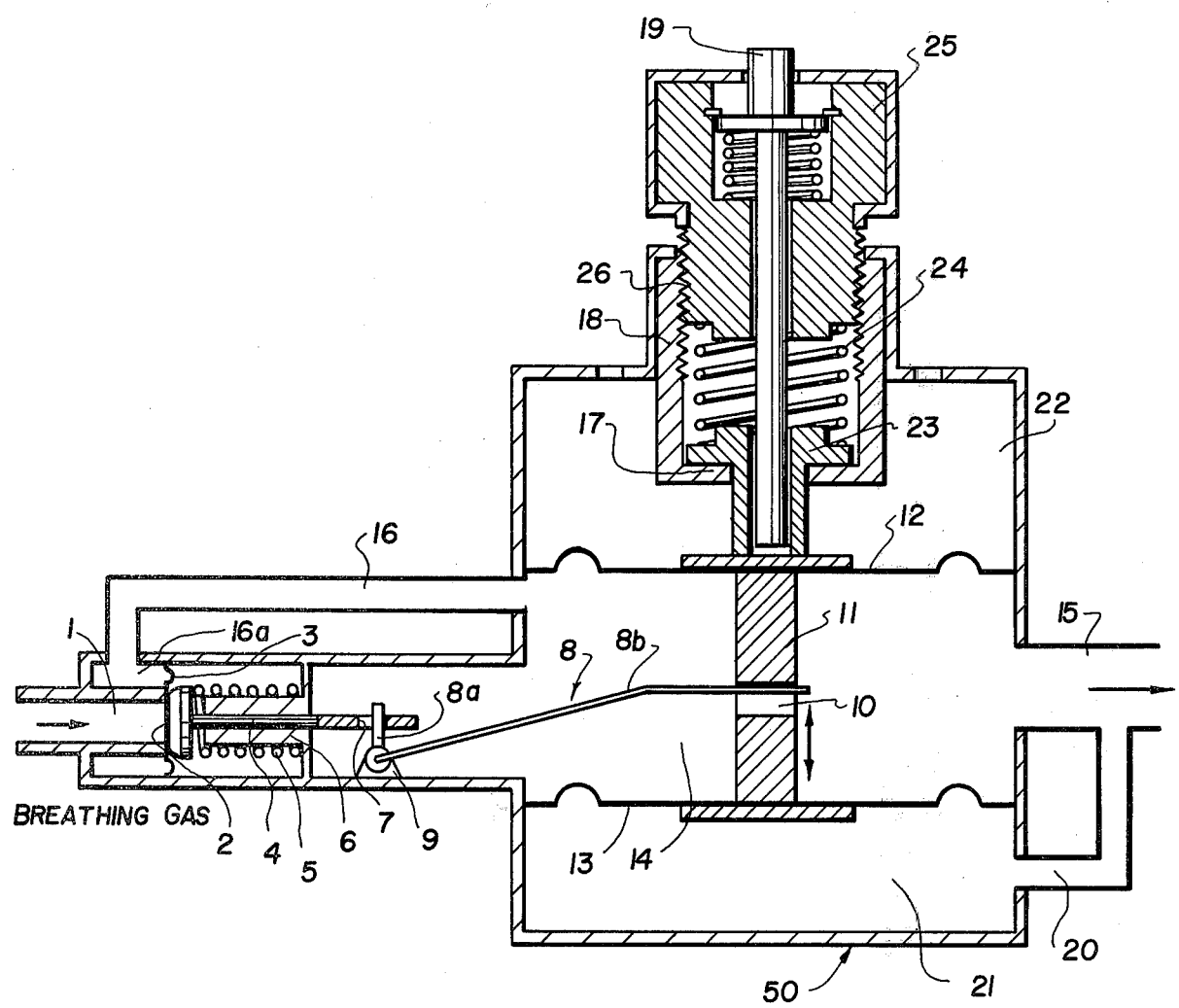

RESPIRATOR VALVE FOR RESPIRATORS

FIELD AND BACKGROUND OF THE INVENTION

The present invention relates to respirators in general and, in particular, to a new and useful respirator valve for respirators in which the breathing phases are controlled by pressure-responsive means, which is actuated by the user's effort to inhale.

DESCRIPTION OF THE PRIOR ART

The respirator valve is a substantial component part of respirators and its purpose is to permit adjustment of the respiratory cycle to the user's condition, thus to the instantaneous breathing frequency and intensity.

A device for artificial respiration is known, in which the nutritive gas, i.e., the breathing gas, is pressed into or removed by suction from the lungs in a pressure-dependent manner. The device comprises an injector and a control space parallel thereto. The nozzle of the injector is connected to the breathing gas supply inlet and the suction side of the injector is connected to the control space and to the lungs of the patient. The diffuser of the injector communicates through a spring-biased excess-pressure valve with the outside air and with the control space through an on-off valve. A diaphragm is provided in the wall of the control space. The diaphragm actuates the on-off valve through a control mechanism comprising a tripping spring. During the expiration phase, i.e., the air removal by suction from the lungs, the on-off valve is closed. Driven by the breathing gas supply at the injector nozzle, the injector removes air by suction from the lungs and discharges it through the spring-biased excess-pressure valve into the open air. Upon emptying of the lungs, the pressure in the lungs and the control space drops, with the result that the diaphragm is switched. Thereby, the on-off valve is opened and the excess-pressure valve closes under the action of its spring. The gas supply at the injector nozzle thereby causes a pressure increase in the system and filling of the lungs.

After the lungs are filled and the predetermined switching pressure is attained, the on-off valve closes again and the expiration phase recommences. This device is not intended to provide a control through the patient's inhalation pulse. The breathing phases are switched by the predetermined differential pressure at the diaphragm. No consideration is given to the patient's condition. The breathing frequency and intensity are not adjusted thereto. (German Pat. No. 916,727).

In another respirator of the prior art, the respiratory cycle is adjusted to the instantaneous breathing frequency and breathing intensity of the patient by means of a pressure-responsive device. In a common housing, this device comprises a pre-pressure chamber and an exhaling chamber which are separated from each other by a pressure-responsive switching mechanism designed as a diaphragm. The pre-pressure chamber is connected to the inlet for the pressurized nutritive, i.e., breathing gas. Means are provided for the supply and venting control through a slot. The exhaling chamber is connected to the exhaling line coming from the patient. The exhaled air is discharged to the outside through a conduit and a check valve. A valve controlled by the position of the switching mechanism opens this conduit and during the exhalation phase and closes it during the inhalation phase.

A switch valve is provided in the breathing gas supply conduit upstream of the pre-pressure chamber, which is also controlled by the switching mechanism and by which, in the inhalation phase started by the patient's effort to inhale, the breathing gas supply to the prepressure chamber is closed and, at the same time, the feed line to the patient is opened. Upon switching over to the exhalation phase, which is done as soon as a definite pressure is produced in the lungs, the feed line to the patient is closed and the breathing gas supply to the pre-pressure chamber is opened.

A satisfactory operation would require an exact control of the preliminary pressure. This is hardly possible, however, with the provided means for controlling the supply of breathing gas and for venting the pre-pressure chamber, which may depend on each other, since the pressure of the breathing gas itself represents a further variable. The escape of breathing gas through the vending slot of the pre-pressure chamber results in an unnecessary, additional consumption of breathing gas. (German Auslegeschrift No. 12 36 135).

SUMMARY OF THE INVENTION

The present invention is directed to a respirator valve which adjusts itself to the user's breathing frequency and breathing intensity by starting the flow of breathing gas in response to the under-pressure pulse caused by the inhalation of the patient and by stopping the gas flow again after the pressure in the lungs has reached a definite, continuously adjustable value.

For this purpose, and in accordance with the invention, two diaphragms are provided; a first or control diaphragm and a second diaphragm, which define a pressure chamber, and which is connected through a connecting line to the lungs and within which the two diaphragms are connected to each other by a connecting rod, and a valve disposed in the breathing gas supply line and actuable by means of a tappet, through a lever mechanism which is movably connected to the connecting rod. The connecting rod is disposed in a chamber which communicates with the outside air and is bounded by the control diaphragm and is aligned with a spring-biased, mushroom-shape member which is axially guided in a threaded bushing. The member bears against a stop surface of the bushing under the action of its spring. The compression strain of the spring is continuously adjustable by an adjusting knob. The second diaphragm bounds a chamber which communicates, through a pressure-equalizing conduit, with the connecting line. The valve comprises a crater-shape valve seat and a valve diaphragm pressed against the seat by a tappet which is biased by a compression spring and guided in a bushing. The lever mechanism is mounted for pivoting in a bearing and has one lever arm movably engaged in a slot of the tappet and the other lever arm movably engaged in a slot of the connecting rod. At the start of the inhalation, the lever arm in the slot of the tappet applies firmly against the slot in the direction of the pressure chamber and the lever arm in the slot of the connecting rod applies firmly against the slot in the direction of the control diaphragm.

The particular advantage of the invention is that this design makes it possible to obtain and secure the desired phase to the exhalation phase in a definite and simple manner, merely by an adjustment means of the adjusting knob. There is no dependency on a preliminary pressure of the breathing gas to be supplied. The inhalation phase is started by a slight under-pressure in the suction system. The large surfaces of the diaphragms ensure a control path which is always satisfactory even under small pressures. As soon as the valve is opened, the entire surface of the valve diaphragm is exposed to the differential pressure. Moreover, the opening of the valve is supported by the diaphragm in the pressure chamber, since here the pressure equalization lags because of the pressure equalization conduit. The slots in the connecting rod and the tappet ensure, in a constructionally simple and trouble-free manner, that the supply of breathing gas is not actually stopped sooner than upon attaining the desired pressure in the lungs. The slots also stabilize the switching system, so that small pressure fluctuations in the respiratory ducts do not cause a premature switching.

According to a development of the invention, a hand-operated actuating knob or member is provided which is guided for axial movement in the adjusting knob and the spring-biased mushroom-shape member and which, in its rest position, is aligned with the connecting rod and after being pushed in, displaces the connecting rod. With this design, any release by the underpressure during inhalation can be effected only if desired, by pressing down the hand-operated knob. This is of importance for emergency situations.

The inventive respirator valve is simple and it may be assembled of only a small number of component parts. The necessary cleaning and disinfection are easy, and there is no risk of maladjustment as in the case of a plurality of adjusting members.

Accordingly, an object of the invention is to provide a respirator valve for respirators with a pressure-responsive control of the breathing pulses of a patient, which comprises a valve housing having a pressure chamber with a connecting line to supply the patient with a breathing gas with first and second control diaphragms closing respective sides of the pressure chamber which are flexible in response to variations of pressure therein and with a connecting member connected between the diaphragms which are moved by variations of pressure to actuate a lever mechanism and shift a valve aligned to a pressurized breathing gas for the controlled inflow of the breathing gas into the pressure chamber.

A further object of the invention is to provide a respirator valve construction which is simple in design, rugged in construction and economical to manufacture.

The various features of novelty which characterize the invention are pointed out with particularly in the claims annexed to and forming a part of this disclosure. For a better understanding of the invention, its operating advantages and specific objects attained by its uses, reference should be had to the accompanying drawing and descriptive matter in which there is illustrated a preferred embodiment of the invention.

BRIEF DESCRIPTION OF THE DRAWING

The only FIGURE of the drawing is a diagrammatic sectional view of a respirator valve constructed in accordance with the invention.

DESCRIPTION OF THE PREFERRED EMBODIMENT

Referring to the drawing in particular, the invention embodied therein, comprises a valve housing, generally designated 50, which includes an interior pressure chamber 14 having control diaphragms 12 and 13 in respective sides thereof which flex in accordance with variations in pressure in the pressure chamber. The flexing of the diaphragms is transmitted to a connecting rod 11 for the purpose of controlling a valve member or tap 4 which is movable to open and close a valve seat 2 of a breathing gas connecting line 1 for furnishing breathing gas under pressure into the pressure chamber 14.

The breathing gas, for example, compressed air or oxygen or another breathable mixture, used for respiration is pressurized (selectively 1 to 6 bar) and applied to valve 1. Valve 1 comprises a crater-shape seat 2 and a valve diaphragm 3. Valve diaphragm 3 is pressed into contact with seat 2 by means of a tappet 4 and a compression spring 5. Tappet 4 is guided in a bushing 6. A lever arm 8a of a lever mechanism 8 is engaged in a slot 7 provided in tappet 4. The lever mechanism is pivotally mounted in a bearing 9. The other lever arm 8b of lever mechanism 8 engages a slot 10 of a connecting rod 11. Connecting rod 11 couples together a control diaphragm 12 and a diaphragm 13. A pressure chamber 14 is formed between diaphragms 12 and 13 and it is connected to the patient through a connecting line 15. Pressure chamber 14 communicates with a connecting line 16 through which, with valve 1 open, the breathing gas is supplied to chamber 14. The line 16 extends to a pressure space 16a on one side of diaphragm 3.

A pressure-equalizing conduit 20 is provided between connecting line 15 and a chamber 21. In a chamber 22, which is open to the outside air, control diaphragm 12 is contacted by a spring-biased, mushroom shape member 23. Member 23 is biased by a compression spring 24 which can be continuously pre-compressed by means of an adjusting knob 25 and a thread 26 provided in a threaded bushing 18. The maximum displacement of member 23 into chamber 22 is limited by a stop surface 17 of threaded bushing 18. A hand-operated knob 19 serves the purpose of manually actuating connecting rod 11.

Connecting line 16 is equipped with further constructional elements which are necessary for varying the respiratory parameters. For example, a gas volume control valve, an injector-gas mixer with a spring-biased check valve, and a flow-controlled pressurized-gas line for an aerosol atomizer (not shown) may be provided.

In the embodiment shown, the device operates as follows:

An underpressure pulse produced by the inhalation of the patient passes through connecting line 15 into pressure chamber 14, and through pressure-equalizing conduit 20 into chamber 21. This produces a differential pressure at control diaphragm 12, because chamber 22 communicates freely with the outside air. There is no pressure difference at diaphragm 13. Due to the differential pressure at control diaphragm 12, connecting rod 11 moves downwardly, in the direction of chamber 21, and lever mechanism 8 is pivoted. Tappet 4 is thereby pushed in the direction against the action of compression spring 5, so that valve diaphragm 3 can be lifted from its seat 2 by the pressure of the breathing gas. This clears the way for the breathing gas through valve 1 to connecting line 16.

During the further motion of valve diaphragm 3, which disengages completely from its seat, the entire surface of the diaphragm becomes exposed to the pressure, whereby, the opening movement is supported. In addition, the opening movement is supported by the fact that at the beginning of the breathing gas flow, diaphragm 13 is loaded at the side of pressure chamber 14 more than at the side of chamber 21. This is obtained by the dimensioning of pressure-equalizing conduit 20 which offers a resistance to the breathing gas flow. Due to this lag in the pressure effect, diaphragm 13 and, thereby, connecting rod 11 keep their lower position a little longer, and the lever mechanism remains in its pivoted position longer. Thus, at the start of inhalation, diaphragm 13 supports the opening operation at valve 1.

Because of the differential pressure at control diaphragm 12, the increasing pressure in pressure chamber 14 causes connecting rod 11 to move in the direction of chamber 22. However, due to slot 10, the closing motion through tappet 4, i.e., the return of valve diaphragm 3 to its seat 2, is not immediately effected. First, the pressure in pressure chamber 14, acting on control diaphragm 12, must overcome the counteracting force exerted by compression spring 24 through mushroom-shape member 23. Only then, the diaphragm system, comprising control diaphragm 12, diaphragm 13 and connecting rod 11, can move in the direction of chamber 22 until the lever arm of lever mechanism 8 abuts the opposite side of slot 10 and is thereby forced to move in the direction in which tappet 4 is pressed against valve diaphragm 3, and diaphragm 3 applies against its seat 2, whereby, the supply of breathing gas to connecting line 16 is interrupted. The breathing gas present in connecting line 16 expands into pressure chamber 14. This removes the pressure from the peripheral surface of valve diaphragm 3 and supports the closing operation at valve 1.

The pressure in pressure chamber 14 is equal to the pressure in the patient's lungs. This pressure is determined by the continuously adjustable counterforce acting on mushroom-shape member 23. The adjustment is made by means of adjusting knob 25. Compression spring 24 determines the amount of adjustment. There is no dependence in the switching system on the preliminary pressure of the breathing gas.

While a specific embodiment of the invention has been shown and described in detail to illustrate the application of the principles of the invention, it will be understood that the invention may be embodied otherwise without departing from such principles.

What is claimed is:

1. A respirator valve for respirators with a pressure-responsive control of the breathing pulses of a patient, comprising a valve housing having a pressure chamber therein with a connecting breathing line to the patient, first and second control diaphragms closing respective sides of said pressure chamber and being flexible in response to pressure variations acting therein, a rigid connecting member connected between said first and second control diaphragms, a pressure breathing gas connection extending into said pressure chamber, a valve seat defined between said pressure breathing gas connection and said pressure chamber, a valve member movable toward and away from said valve seat to close and open it, a lever mechanism connected between said valve member and said connecting member movable by variations of movement of said connecting member due to variations in the patient's efforts to inhale and connected to said valve member to shift said valve member to open and close the valve seat for regulating the pressure into said pressure chamber.

2. A respirator valve for respirators with a pressure-responsive control of the breathing pulses of a patient, comprising a valve housing having a pressure chamber therein with a connecting breathing line to the patient, first and second control diaphragms closing respective sides of said pressure chamber and being flexible in response to pressure variations acting therein, a rigid connecting member connected between said first and second control diaphragms, a pressure breathing gas connection extending into said pressure chamber, a valve seat defined between said pressure breathing gas connection and said pressure chamber, a valve member movable toward and away from said valve seat to close and open it, a lever mechanism connected between said valve member and said connecting member movable by variations of movement of said connecting member due to variations in the patient's efforts to inhale and connected to said valve member to shift said valve member to open and close the valve seat for regulating the pressure into said pressure chamber, said housing having a chamber bounding said pressure chamber on an opposite side of said first control diaphragm which is connected to atmosphere, a mushroom-shape member adapted to bear against said diaphragm, spring means biasing said mushroom-shape member against said diaphragm housing having a threaded bore aligned with with mushroom-shape member, an adjustment knob threaded into said bore and adapted to bear against said biasing means for varying the force of said spring means acting on said diaphragm, and stop means located in said housing for stopping the movement of said mushroom-shape member in a direction toward said diaphragm.

3. A respirator valve for respirators, according to claim 2, including a chamber bounding said second diaphragm located in said housing and a pressure-equalizer extending from said chamber bounding said second diaphragm to said connecting breathing line to the patient.

4. A respirator valve for respirators with a pressure-sensitive control of the breathing pulses of a patient, comprising a valve housing having a pressure chamber therein with a connecting breathing line to the patient, first and second control diaphragms closing respective sides of said pressure chamber and being flexible in response to pressure variations acting therein, a rigid connecting member connected between said first and second control diaphragms, a pressure breathing gas connecting extending into said pressure chamber, a valve seat defined between said pressure breathing gas connection and said pressure chamber, a valve member movable toward and away from said valve seat to close and open it, a lever mechanism connected between said valve member and said connecting member movable by variations of movement of said connecting member due to variations in the patient's effort to inhale and connected to said valve member to shift said valve member to open and close the valve seat for regulating the pressure into said pressure chamber, said housing including a diaphragm closing said valve seat, said valve member comprising a tappet engageable against said valve diaphragm and spring means biasing said tappet toward said diaphragm.

5. A respirator valve for respirators, according to claim 4, including means pivotally supporting said lever mechanism in said pressure chamber, said lever mechanism comprising a double-arm lever having a first arm portion engageable with said connecting rod and a second arm portion engageable with said valve member, said valve member having an arm portion with a slot in which said second arm portion extends whereby, at the beginning of inhalation, the first lever arm portion firmly applies against the end of said slot in a direction toward said pressure chamber, said connecting rod having a slot therein, said second arm portion applying against the end of said slot in the direction of said first control diaphragm.

6. A respirator valve for respirators with a pressure-sensitive control of the breathing pulses of a patient, comprising a valve housing having a pressure chamber therein with a connecting breathing line to the patient, first and second control diaphragms closing respective sides of said pressure chamber and being flexible in response to pressure variations acting thereon, a rigid connecting member connected between said first and second control diaphragms, a pressure breathing gas connection extending into said pressure chamber, a valve seat defined between said pressure breathing gas connection and said pressure chamber, a valve member movable toward and away from said valve seat to close and open it, a lever mechanism connected between said valve member and said connecting member movable by variations of movement of said connecting member due to variations in the patient's efforts to inhale and connected to said valve member to shift said valve member to open and close the valve seat for regulating the pressure into said pressure chamber, and a member adapted to bear against said first control valve aligned with said connecting rod and a knob means threadable in said housing for adjusting said spring means in respect to said diaphragm.

* * * * *